(12) United States Patent
Taniguchi

(10) Patent No.: US 11,607,121 B2
(45) Date of Patent: Mar. 21, 2023

(54) MOUNTING MEMBER AND ENDOSCOPIC DEVICE

(71) Applicant: Sony Olympus Medical Solutions Inc., Tokyo (JP)

(72) Inventor: Takuya Taniguchi, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 156 days.

(21) Appl. No.: 17/151,670

(22) Filed: Jan. 19, 2021

(65) Prior Publication Data

US 2021/0282629 A1  Sep. 16, 2021

(30) Foreign Application Priority Data

Mar. 13, 2020  (JP) .............................. JP2020-044611

(51) Int. Cl.
    *A61B 1/04* (2006.01)
    *A61B 1/00* (2006.01)
    *A61B 1/05* (2006.01)

(52) U.S. Cl.
    CPC .......... *A61B 1/042* (2013.01); *A61B 1/00042* (2022.02); *A61B 1/00112* (2013.01); *A61B 1/053* (2013.01)

(58) Field of Classification Search
    CPC ............ A61B 1/00101; A61B 1/00112; A61B 1/00105; A61B 1/053
    See application file for complete search history.

(56) References Cited

U.S. PATENT DOCUMENTS

| 2014/0111634 A1* | 4/2014 | Mueckl .............. A61B 1/00105 348/82 |
| 2019/0192818 A1* | 6/2019 | Koda ..................... A61B 1/042 |
| 2021/0100431 A1* | 4/2021 | Shainwald ........... A61B 1/0052 |

* cited by examiner

*Primary Examiner* — Aaron B Fairchild
(74) *Attorney, Agent, or Firm* — Xsensus LLP

(57) ABSTRACT

A mounting member includes: a body portion provided in a camera head including an image sensor, the body portion being rotatable about a first axis that passes through the body portion and connectable with an endoscope; a locking protrusion provided in the body portion and configured to lock with the endoscope; a detachable button configured to be movable with respect to the body portion and control attachment and detachment of the endoscope to and from the body portion; and a spring whose load applied to the locking protrusion changes according to an advancing/retreating operation of the detachable button with respect to the body portion. The detachable button includes a sliding portion extending in an advancing/retreating direction with respect to the body portion and configured to slide with respect to the body portion. The body portion includes a guide portion configured to guide a moving direction of the sliding portion.

18 Claims, 9 Drawing Sheets

MOUNTING MEMBER AND ENDOSCOPIC DEVICE

CROSS-REFERENCE TO RELATED APPLICATION

This application claims priority from Japanese Application No. 2020-044611, filed on Mar. 13, 2020, the contents of which are incorporated by reference herein in its entirety.

BACKGROUND

The present disclosure relates to a mounting member used in an endoscope and an endoscopic device.

In the medical field and industrial field, an endoscopic device that observes the inside of a subject such as a human and a mechanical structure is known (see, for example, JP 2000-227559 A). The endoscopic device described in JP 2000-227559 A includes an endoscope (optical telescope) that takes and emits a subject image inside a subject and endoscope camera head (TV camera) that holds the endoscope and captures the subject image emitted from the endoscope. The endoscope is held to be rotatable about an internally set optical axis with respect to the endoscope camera head.

The endoscope camera head includes a mounting member and a camera head body. The mounting member has a bottomed cylindrical shape to which an eyepiece unit of the endoscope may be fitted. A part of the eyepiece unit is accommodated in a concave portion of the mounting member. In the concave portion of the mounting member, a locking protrusion that locks with the eyepiece unit is provided so as to protrude in a freely advancing and retreating manner. A regulation state of the locking protrusion according to the attachment and detachment of the endoscope (eyepiece unit) may be switched, for example, by pressing a detachable button provided on the mounting member. Specifically, a spring member is provided between the detachable button and the locking protrusion, and the spring member is deformed by pushing the detachable button so that the movable amount of the locking protrusion that advances or retreats with respect to the concave portion changes. When the detachable button is not pressed, a load from the spring member regulates the locking protrusion in a direction of projecting toward the inside of the concave portion, and the detachment of the eyepiece unit from the mounting member is suppressed.

SUMMARY

By the way, the mounting member forms a body portion by fixing two stacked members with a screw, and the locking protrusion, the detachable button, and the spring member are accommodated inside the body portion. Meanwhile, it has been desired to reduce the number of parts constituting the mounting member in order to reduce the weight and improve the assembleability.

There is a need for a mounting member used in an endoscope and an endoscopic device capable of reducing the number of parts.

According to one aspect of the present disclosure, there is provided a mounting member including: a body portion provided in a camera head including an image sensor, the body portion being rotatable about a first axis that passes through the body portion and connectable with an endoscope; a locking protrusion provided in the body portion and configured to lock with the endoscope; a detachable button configured to be movable with respect to the body portion and control attachment and detachment of the endoscope to and from the body portion; and a spring whose load applied to the locking protrusion changes according to an advancing/retreating operation of the detachable button with respect to the body portion, wherein the detachable button includes a sliding portion extending in an advancing/retreating direction with respect to the body portion and configured to slide with respect to the body portion, and the body portion includes a guide portion configured to guide a moving direction of the sliding portion.

DETAILED DESCRIPTION

Hereinafter, modes for carrying out the present disclosure (hereinafter, referred to as "embodiments") will be described in detail with reference to the drawings. Incidentally, the present disclosure is not limited by the following embodiments. In addition, the respective drawings referred to in the following description merely illustrate shapes, sizes, and positional relationships in a schematic manner to such an extent that contents of the present disclosure may be understood. That is, the present disclosure is not limited to only the shapes, sizes, and positional relationships illustrated in the respective drawings. Further, the same reference sign will be assigned to the same components in the description of the drawings.

Schematic Configuration of Endoscopic Device

Figure 1:
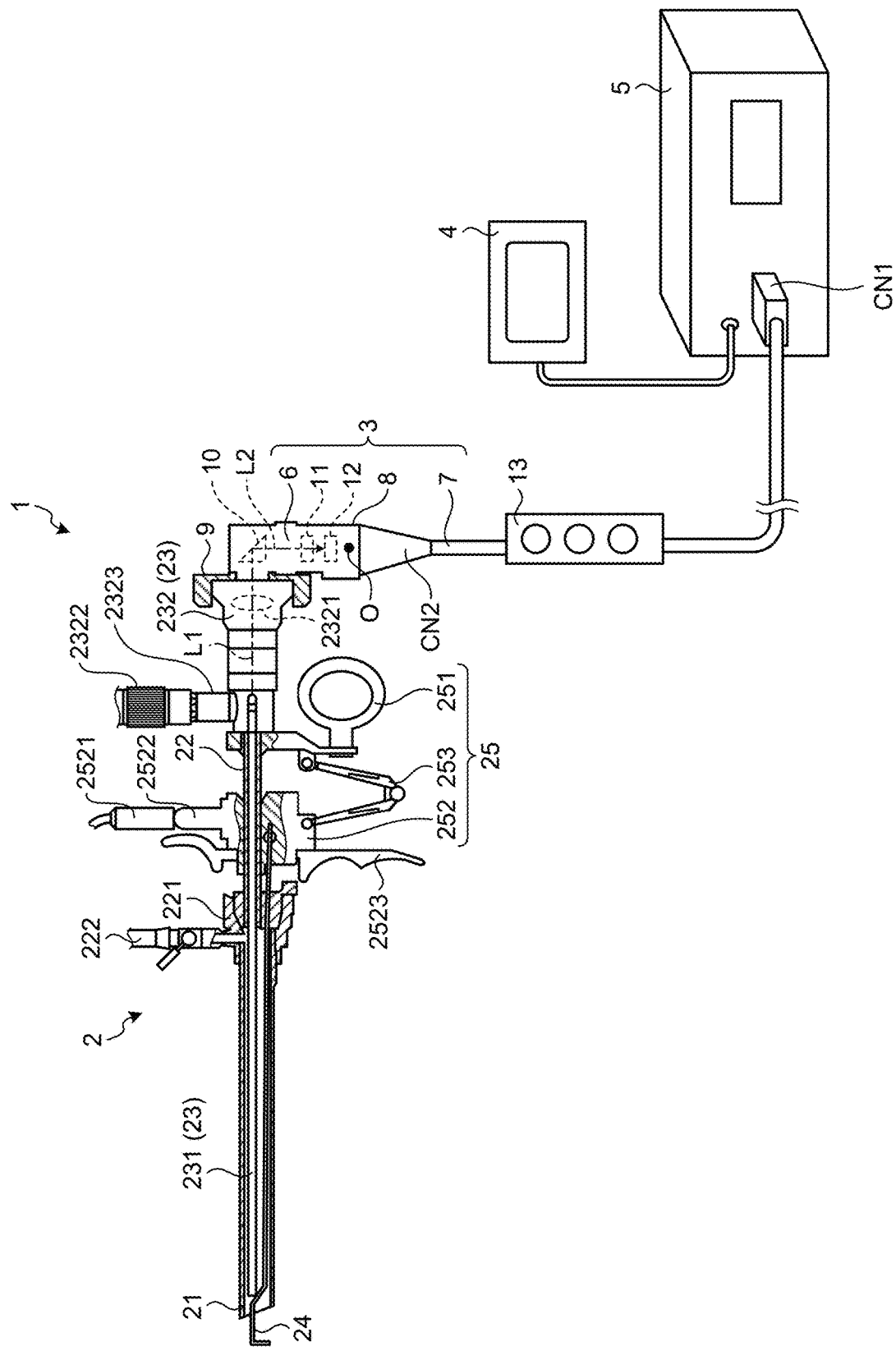
FIG. 1 is a view illustrating a schematic configuration of an endoscopic device according to an embodiment.

FIG. 1 is a view illustrating a schematic configuration of an endoscopic device according to an embodiment.

An endoscopic device 1 illustrated in FIG. 1 is a device used in the medical field to treat (for example, resect) a living tissue while observing the inside of a living body. As illustrated in FIG. 1, the endoscopic device 1 includes a resectoscope 2, an endoscope imaging device 3, a display device 4, and a control device 5.

Configuration of Resectoscope

The resectoscope 2 may be inserted into a living body, take a subject image, and treat a living tissue. As illustrated in FIG. 1, the resectoscope 2 includes a sheath 21, a guide tube 22, an endoscope 23, a resecto-electrode member 24, and a handle 25.

The sheath 21 has a cylindrical shape and is a portion to be inserted into a living body. The guide tube 22 has an outer diameter dimension smaller than an inner diameter dimension of the sheath 21, and is inserted into the sheath 21. A distal end side (left side in FIG. 1) of the guide tube 22 is fixed to the sheath 21 via an attachment member 221. Here, the attachment member 221 is provided with a water supply port 222 configured to inject a liquid into the sheath 21 and supply the liquid from a distal end of the sheath 21.

The endoscope 23 is a portion that takes a subject image, and includes an insertion unit 231 and an eyepiece unit 232 as illustrated in FIG. 1.

The insertion unit 231 is fixed in the guide tube 22 and inserted into the sheath 21. An optical system, which includes one or a plurality of lenses and condenses a subject image, is provided in the insertion unit 231.

The eyepiece unit 232 is connected to a proximal end (right end in FIG. 1) of the insertion unit 231. An eyepiece optical system 2321, which emits a subject image condensed by the optical system in the insertion unit 231 to the outside from the eyepiece unit 232, is provided in the eyepiece unit 232. The eyepiece unit 232 is formed in a tapered shape whose diameter increases toward the right side in FIG. 1, and the endoscope imaging device 3 is detachably connected to an enlarged diameter portion thereof.

Here, the eyepiece unit 232 is provided with a light source connector 2323 configured to connect a light guide 2322. That is, light supplied from a light source device (not illustrated) to the light guide 2322 is supplied to the insertion unit 231 via the eyepiece unit 232. The light supplied to the insertion unit 231 is emitted from a distal end of the insertion unit 231 and is emitted inside a living body. The light (subject image), which has been emitted inside the living body and reflected inside the living body, is emitted from the eyepiece unit 232 via the optical system in the insertion unit 231 and the eyepiece optical system 2321.

The resecto-electrode member 24 is inserted into the sheath 21 via the attachment member 221 and has a distal end protruding from the distal end of the sheath 21. A distal end portion of the resecto-electrode member 24 comes into contact with a living tissue, and treats the living tissue with a high-frequency current.

The handle 25 is a portion where a doctor or the like grips the resectoscope 2 and operates the resecto-electrode member 24. As illustrated in FIG. 1, the handle 25 includes a fixing ring 251, a slider 252, and a spring member 253.

The fixing ring 251 is a portion on which a doctor or the like hooks the thumb, and is fixed to the guide tube 22.

The slider 252 into which the guide tube 22 is inserted is movable in the left-right direction in FIG. 1 along the guide tube 22. As illustrated in FIG. 1, the resecto-electrode member 24 is fixed to the slider 252. That is, the resecto-electrode member 24 moves back and forth inside the sheath 21 in the left-right direction in FIG. 1 along with the movement of the slider 252. In addition, the slider 252 is provided with a power supply connector 2522 configured to connect a high frequency power cord 2521 connected to a high frequency power supply (not illustrated). The power supply connector 2522 is electrically connected to the resecto-electrode member 24 via a lead wire (not illustrated). Further, as illustrated in FIG. 1, the slider 252 is provided with a finger hook member 2523 configured for the doctor or the like to hook a finger other than the thumb and move the slider 252 (move the resecto-electrode member 24 back and forth).

The spring member 253 has a substantially U-shape and has one end attached to the fixing ring 251 and the other end attached to the slider 252. The spring member 253 biases the slider 252 to a side separating from the fixing ring 251. That is, the doctor or the like hooks the fingers on the fixing ring 251 and the finger hook member 2523, and pulls the finger hook member 2523 against a biasing force of the spring member 253, thereby moving the slider 252 to the right side in FIG. 1 (moving the resecto-electrode member 24 to the right side in FIG. 1). On the other hand, the slider 252 (resecto-electrode member 24) moves to the left side in FIG. 1 due to the biasing force of the spring member 253 when the doctor or the like releases the finger from the finger hook member 2523.

The endoscope imaging device 3 is detachably connected to the eyepiece unit 232 of the resectoscope 2 (endoscope 23). The endoscope imaging device 3 captures a subject image (subject image emitted from the eyepiece unit 232) taken by the endoscope 23 under the control of the control device 5, and outputs an image signal (RAW signal) obtained by this imaging. This image signal is, for example, an image signal of 4K or higher. The endoscope imaging device 3 includes an endoscope camera head 6 and a cable 7. Incidentally, a detailed configuration of the endoscope camera head 6 will be described later.

The display device 4 is configured using a display using a liquid crystal or an organic electro luminescence (EL), or the like. The display device 4 displays an observation image based on a video signal from the control device 5 under the control of the control device 5.

The control device 5 is configured using a memory and a processor such as hardware of a field programmable gate array (FPGA) or a central processing unit (CPU). The control device 5 performs the overall control of operations of the endoscope imaging device 3, the display device 4, and the light source device (not illustrated). For example, the control device 5 performs predetermined image processing on the image signal (RAW signal) output from the endoscope imaging device 3 to generate a video signal for display, and displays an observation image based on this video signal on the display device 4.

Configuration of Endoscope Camera Head

Next, a detailed configuration of the endoscope camera head 6 will be described. As illustrated in FIG. 1, the endoscope camera head 6 and the cable 7 are provided.

The endoscope camera head 6 is a portion that is detachably connected to the eyepiece unit 232. As illustrated in FIG. 1, the endoscope camera head 6 includes a casing 8, a mounting member 9 (coupler), a prism 10, a lens unit 11, and an imaging unit 12.

The casing 8 is a casing that accommodates the prism 10, the lens unit 11, and the imaging unit 12 therein. In addition, the casing 8 has a lever 8a that switches a locked state with the eyepiece unit 232.

The mounting member 9 has a bottomed cylindrical shape into which the eyepiece unit 232 may be fitted. The mounting member 9 is regulated from moving in a direction of a first axis L1 with respect to the casing 8, and is rotatable with respect to the casing 8 about the first axis L1. Incidentally, a detailed configuration of the mounting member 9 will be described later.

The prism 10 is arranged on an in-casing optical axis L2 on the first axis L1, and deflects a traveling direction of the subject image taken by the endoscope 23. Specifically, the prism 10 deflects the traveling direction of the subject image emitted from the eyepiece unit 232 and taken in the casing 8 via an optical element (not illustrated) by approximately 90° to cause the subject image to travel along the in-casing optical axis L2.

The lens unit 11 is arranged on the in-casing optical axis L2. The lens unit 11 is configured using one or a plurality of lenses, and forms the subject image passing through the prism 10 on an imaging surface of the imaging unit 12. In addition, the lens unit 11 is provided with an optical zooming mechanism (not illustrated) that moves one or more lenses to change an angle of view under the control of the control device 5 or an operating unit 13, a focusing mechanism (not illustrated) that changes a focal point, and the like.

The imaging unit 12 is arranged on the in-casing optical axis L2. Then, the imaging unit 12 captures the subject image formed by the lens unit 11 under the control of the control device 5. The imaging unit 12 is configured using a sensor chip on which an imaging element (not illustrated), such as a charge coupled device (CCD) and a complementary metal oxide semiconductor (CMOS), which receives the subject image formed by the lens unit 11 and converts the subject image into an electrical signal, a signal processing unit (not illustrated) which performs signal processing (A/D conversion or the like) on the electrical signal (analog signal) from this imaging element to output an image signal, and the like are integrally formed, and outputs the image signal (RAW signal (digital signal)) after A/D conversion. Incidentally, the signal processing unit described above may be a separate body without being integrally formed with the imaging element.

In this manner, the endoscope camera head 6 is configured to be rotatable about the first axis L1 with respect to the eyepiece unit 232 of the endoscope 23 via the mounting member 9. In addition, the endoscope camera head 6 is configured so as to have a center of gravity O shifted from the first axis L1 (rotation center axis with respect to the eyepiece unit 232). Then, the endoscope camera head 6 is configured to rotate about the first axis L1 regardless of the rotation of the resectoscope 2 about the first axis L1 and take a posture in which the in-casing optical axis L2 set in the casing 8 extends along the vertical direction (posture in which the center of gravity O is located below the first axis L1).

The cable 7 has one end detachably connected to the control device 5 via a connector CN1, and the other end detachably connected to the endoscope camera head 6 via a connector CN2. The cable 7 transmits the image signal output from the endoscope camera head 6 to the control device 5, and also transmits each of a control signal, a synchronization signal, a clock, power, and the like output from the control device 5 to the endoscope camera head 6. Incidentally, in the transmission of the image signal from the endoscope camera head 6 to the control device 5 via the cable 7, the image signal may be transmitted as an optical signal or may be transmitted as an electrical signal. The same applies to the transmission of the control signal, the synchronization signal, and the clock from the control device 5 to the endoscope camera head 6 via the cable 7. In addition, as illustrated in FIG. 1, the cable 7 is provided with an operating unit 13 that receives instructions from the doctor or the like for various operations (for example, image quality adjustment (white balance adjustment, brightness adjustment, and the like) of the observation image) and an instruction to change the angle of view or the focal point of the lens unit 11).

Configuration of Mounting Member

Next, the detailed configuration of the mounting member 9 will be described.

Figure 2:
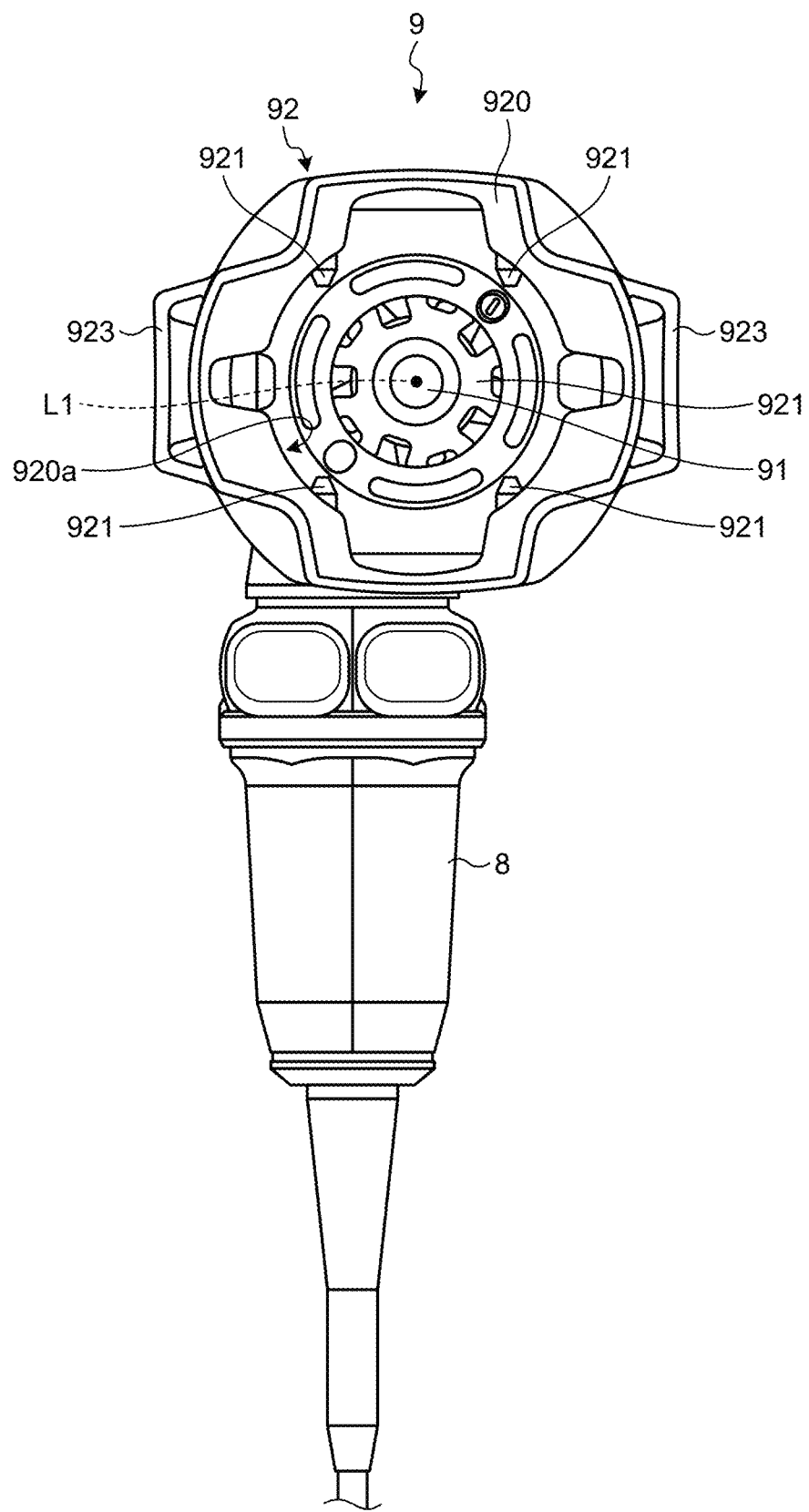
FIG. 2 is a plan view illustrating a configuration of a main part of the endoscopic device illustrated in FIG. 1, and is a plan view illustrating configurations of a camera head body and a mounting member.
Figure 3:
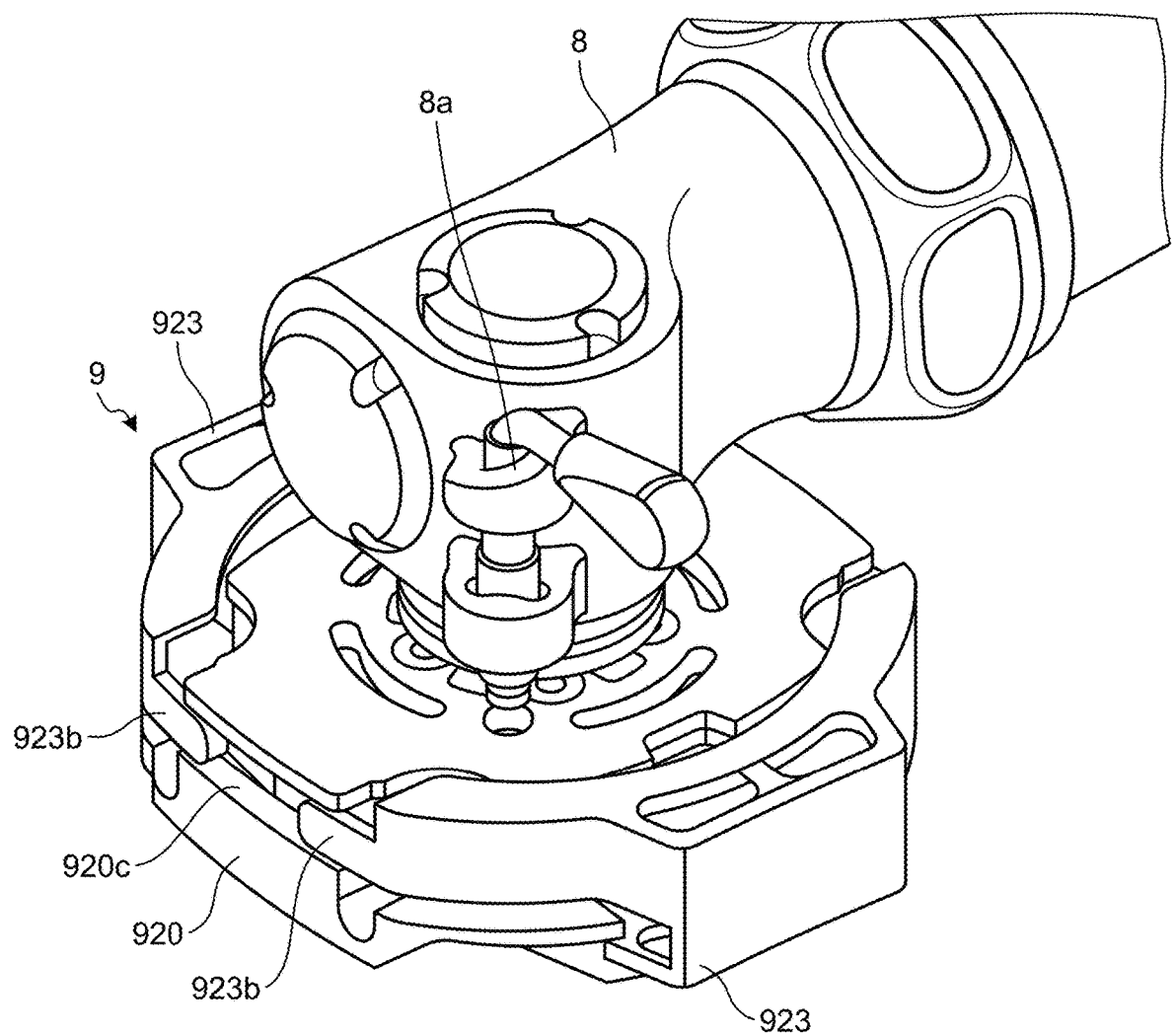
FIG. 3 is a view illustrating a connection portion between the camera head body and the mounting member.
Figure 4:
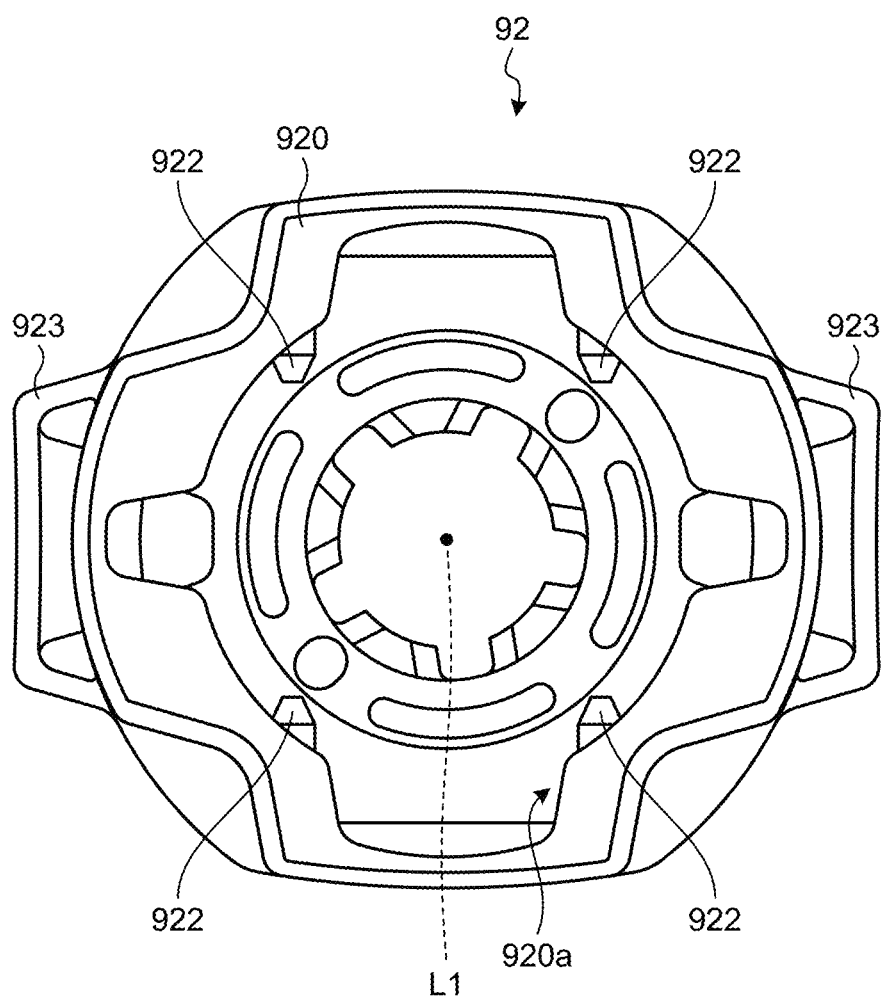
FIG. 4 is a plan view (Part 1) illustrating a configuration of a second member of the mounting member according to the embodiment.
Figure 5:
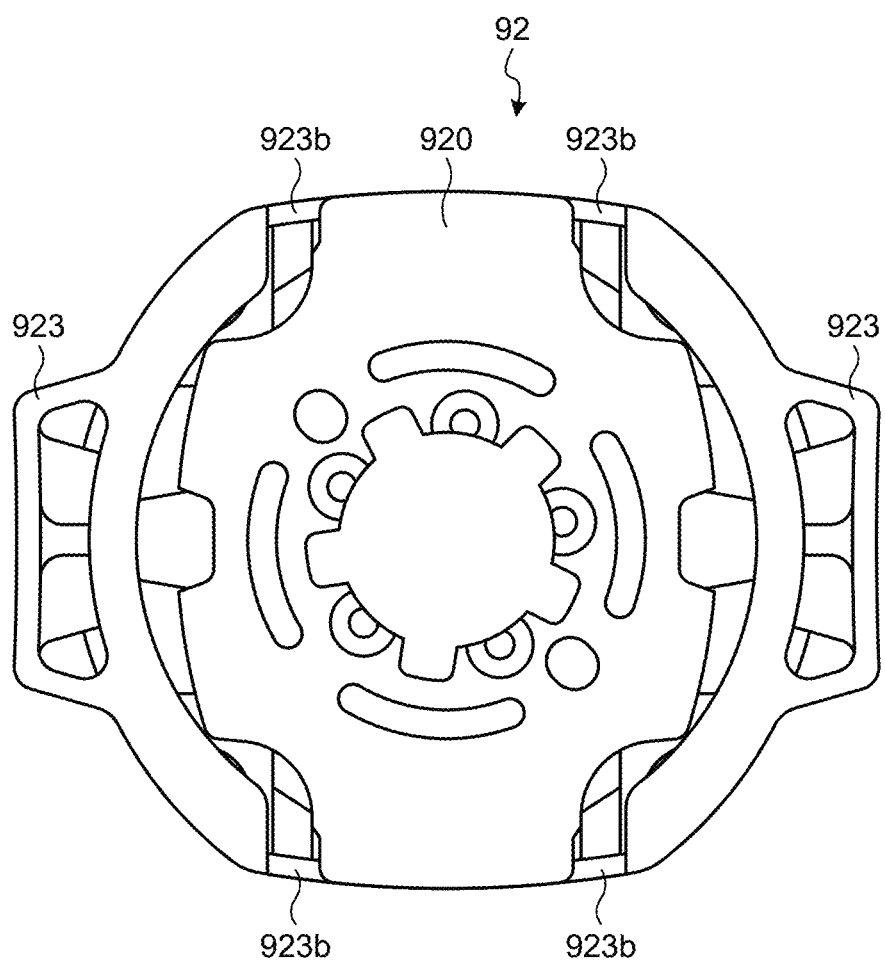
FIG. 5 is a plan view (Part 2) illustrating the configuration of the second member of the mounting member according to the embodiment.
Figure 6:
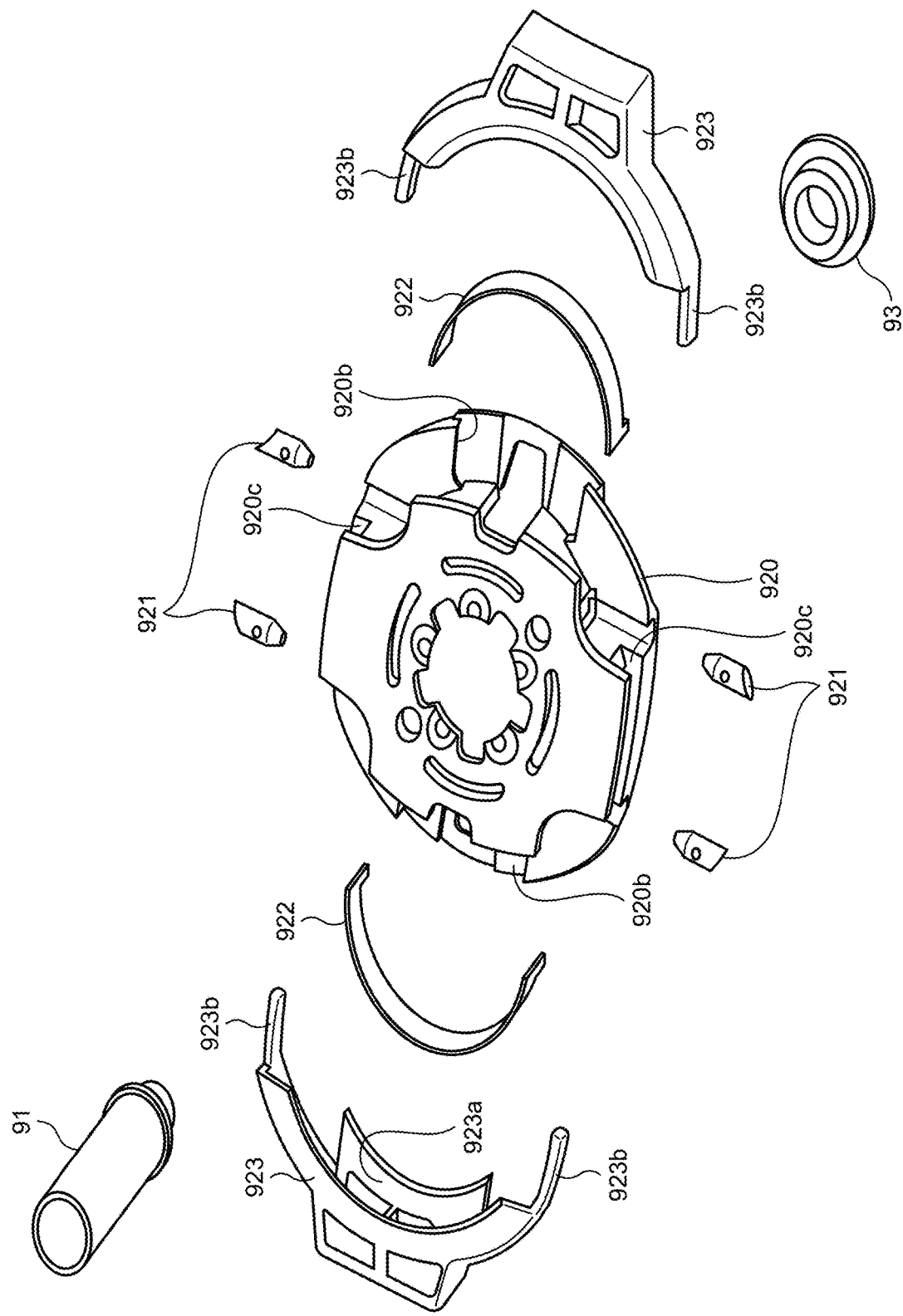
FIG. 6 is an exploded perspective view (Part 1) of the mounting member according to the embodiment.
Figure 7:
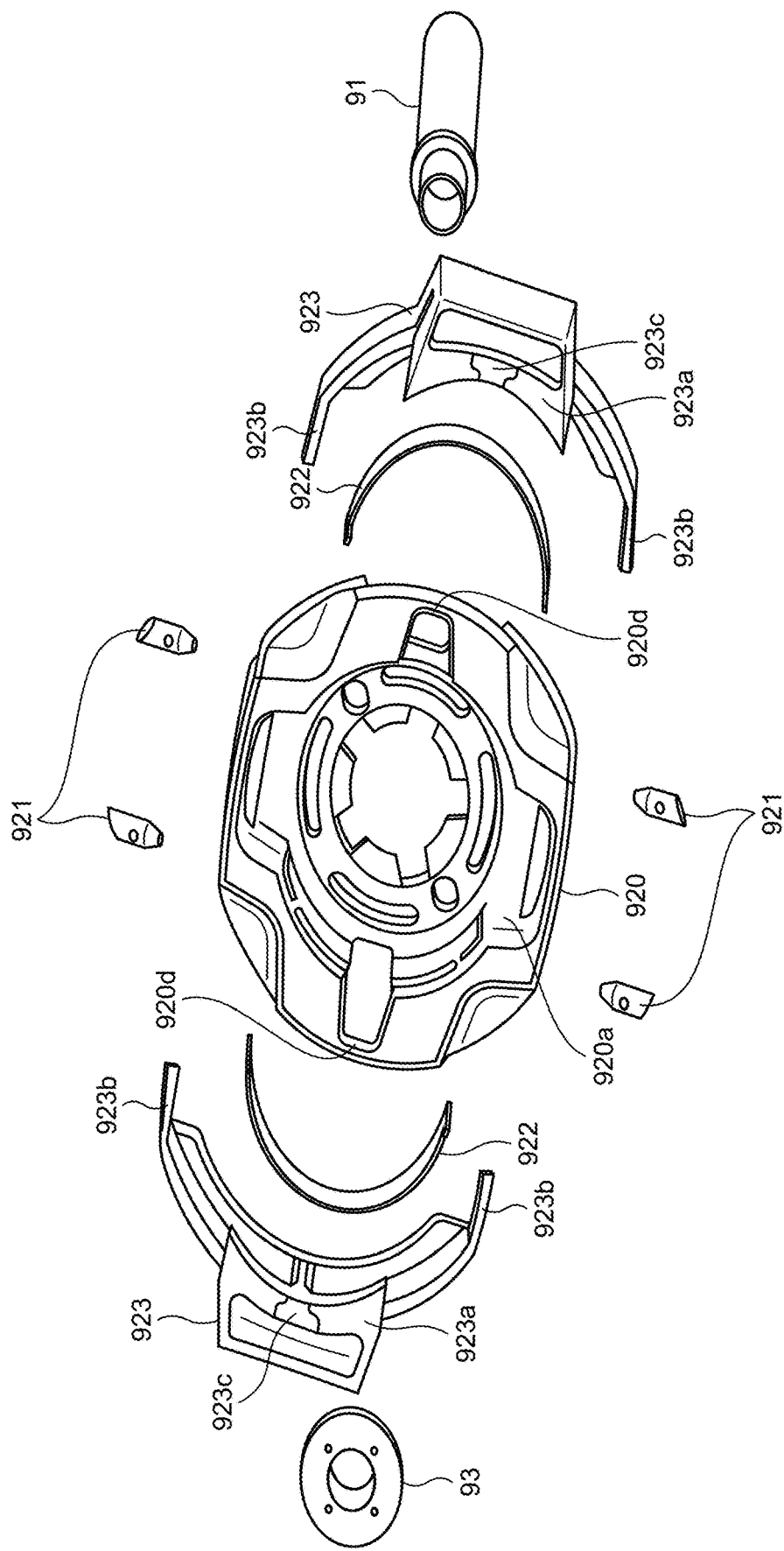
FIG. 7 is an exploded perspective view (Part 2) of the mounting member according to the embodiment.

FIG. 2 is a plan view illustrating a configuration of a main part of the endoscopic device illustrated in FIG. 1, and is a plan view illustrating configurations of the camera head body and the mounting member. FIG. 3 is a view illustrating a connection portion between the camera head body and the mounting member. FIGS. 4 and 5 are plan views illustrating a configuration of a second member of the mounting member according to the embodiment. FIGS. 6 and 7 are exploded perspective views of the mounting member according to the embodiment. Incidentally, FIGS. 4 and 5 are views as viewed from opposite directions to each other, specifically, opposite directions to each other in the direction of the first axis L1. In addition, FIG. 7 is an exploded perspective view as viewed from a direction different from that of FIG. 6.

The mounting member 9 includes a first member 91, a second member 92, and a regulating member 93.

Configuration of First Member

First, a configuration of the first member 91 will be described.

The first member 91 is provided on the endoscope camera head 6 having the imaging unit 12. Specifically, the first member 91 is a member configured to attach the mounting member 9 to the casing 8 and a member configured to support the rotation of the second member 92. The first member 91 extends in the direction of the first axis L1, and has an end portion on a side opposite to a side connected to the casing 8 being connected to the regulating member 93.

Configuration of Second Member

Next, a configuration of the second member 92 will be described.

The second member 92 may rotate about the first axis L1 passing through the first member 91, and the endoscope 23 may be connected to the second member 92. The second member 92 includes a body portion 920, locking protrusions 921, spring members 922, and detachable buttons 923.

The body portion 920 forms a casing of the second member 92.

The body portion 920 has a dish shape having a concave portion 920a that has a hole shape to accommodate the eyepiece unit 232. The body portion 920 has a first guide portion 920b and second guide portions 920c that guide a moving direction of the detachable button 923. Two second guide portions 920c are formed with the first axis L1 interposed therebetween. Incidentally, in the body portion 920, a hole (not illustrated) from which the locking protrusion 921 protrudes is formed in the concave portion 920a.

Each of the first guide portion 920b and the second guide portion 920c has a concave shape extending along the moving direction of the detachable button 923. The moving direction of the detachable button 923 corresponds to an advancing/retreating direction of the detachable button 923 with respect to the body portion 920.

The body portion 920 holds the detachable button 923 so that the detachable button 923 is capable of advancing and retreating with respect to the body portion 920. At this time, the detachable button 923 is biased by the spring member 922 in a direction of protruding to the outer surface of the body portion 920.

The locking protrusion 921 presses the endoscope 23 (eyepiece unit 232) toward the first axis L1 when the endoscope 23 is connected. In the present embodiment, four locking protrusions 921 are provided. The locking protrusions 921 are provided at positions where distal ends of two locking protrusions 921 forming a pair face each other. The locking protrusion 921 is biased by the spring member 922 so as to be movable in directions of coming close to or separating from the paired locking protrusion 921, and abuts on an outer peripheral surface of the eyepiece unit 232 fitted inside the mounting member 9 and presses the eyepiece unit 232 toward a bottom of the concave portion 920a of the body portion 920.

The spring member 922 is configured using a leaf spring formed by bending a strip-shaped member. The spring member 922 has both end portions on which the respective locking protrusions 921 abut, and biases each of the locking protrusions 921 in the direction of coming close to the opposing locking protrusion 921. In addition, in the mounting member 9, the spring member 922 is arranged between the body portion 920 and the detachable button 923. The spring member 922 biases the detachable button 923 in the direction of protruding from the body portion 920.

The detachable button 923 extends in an arc shape and is attached to be movable with respect to the body portion 920. The detachable button 923 sandwiches the spring member 922 with the body portion 920. The detachable button 923 applies a load, generated when the mounting member 9 is pressed toward the first axis L1 from the outside, to the spring member 922 to expand the spring member 922. As the spring member 922 expands, the biasing force of the spring member 922 on the locking protrusion 921 is reduced.

The detachable button 923 includes a first sliding portion 923a that extends in the advancing/retreating direction with respect to the body portion 920 and slides along the first guide portion 920b, and two second sliding portions 923b that extend in the advancing/retreating direction with respect to the body portion 920 and move along the second guide portions 920c.

The first sliding portion 923a has a width equivalent to a notch width of the first guide portion 920b, and has a plate shape extending in the moving direction of the detachable button 923 (here, the direction orthogonal to the first axis L1). A width direction referred to herein is orthogonal to the first axis L1. As the first sliding portion 923a slides along the first guide portion 920b, the movement in the direction of the first axis L1 is guided.

The second sliding portion 923b extends in a columnar shape that is movable along a recess of the second guide portion 920c. The second sliding portions 923b are each provided at each of both ends of the detachable button 923. The detachable button 923 sandwiches the body portion 920 between the two second sliding portions 923b.

Figure 8:
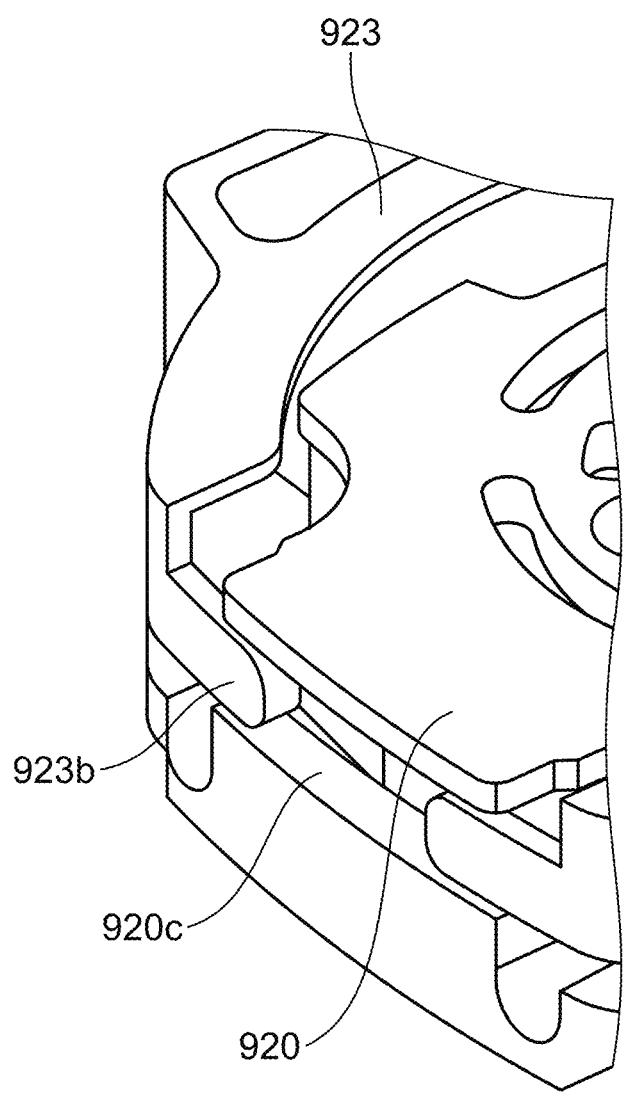
FIG. 8 is an enlarged view illustrating a configuration of a main part of the mounting member according to the embodiment.

FIG. 8 is an enlarged view illustrating the configuration of the main part of the mounting member according to the embodiment. The second sliding portion 923b of one of the detachable buttons 923 enters the second guide portion 920c from one end side, and the second sliding portion 923b of the other detachable button 923 enters from the other end side. The second sliding portion 923b slides on the second guide portion 920c so that the moving direction of the detachable button 923 is guided. In addition, the second sliding portion 923b slides along a wall surface of the second guide portion 920c so that the rattling of the detachable button 923 with respect to the body portion 920 is suppressed. In particular, it is possible to suppress rattling in a direction orthogonal to the main surface (the surface having the largest area) of the first sliding portion 923a.

Figure 9:
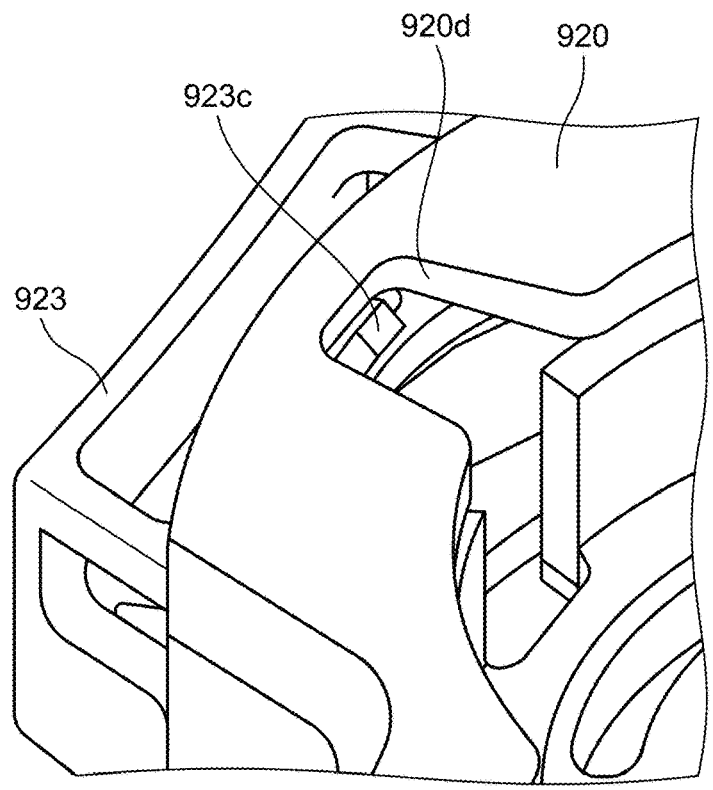
FIG. 9 is an enlarged view illustrating the configuration of the main part of the mounting member according to the embodiment.

FIG. 9 is an enlarged view illustrating the configuration of the main part of the mounting member according to the embodiment, and is a view for describing a locked state between the body portion 920 and the detachable button 923.

Figure 10:
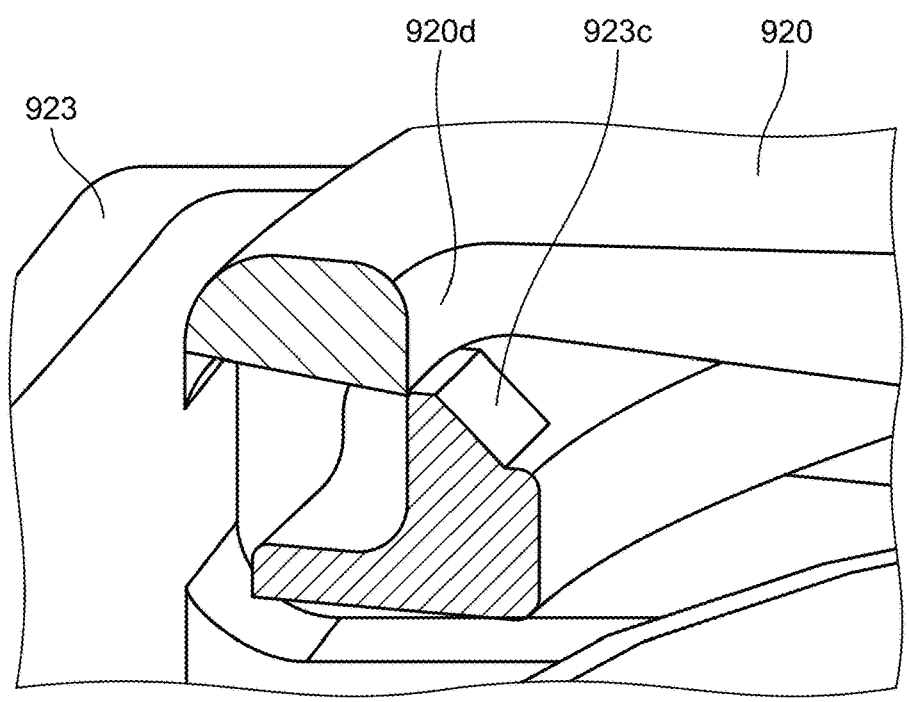
FIG. 10 is a partial cross-sectional view illustrating the configuration of the main part of the mounting member according to the embodiment.

FIG. 10 is a partial cross-sectional view illustrating the configuration of the main part of the mounting member according to the embodiment, and is a view for describing the locked state between the body portion 920 and the detachable button 923.

As one of the body portion 920 and the detachable button 923 is locked with the other, the detachable button 923 is prevented from being detached from the body portion 920. In the present embodiment, the detachable button 923 is provided with a protruding portion 923c, and the protruding portion 923c is locked with the body portion 920 to prevent the detachable button 923 from being detached from the body portion 920. The protruding portion 923c protrudes in the moving direction of the detachable button 923. The protruding portion 923c abuts on a notched portion 920d formed in the body portion 920 to prevent the detachable button 923 from being detached from the body portion 920. The amount of movement of the detachable button 923 with respect to the body portion 920 may be adjusted by adjusting formation positions of the protruding portion 923c and the notched portion 920d. At this time, the protruding portion 923c is provided on the opposite side of the first sliding portion 923a in the thickness direction of the detachable button 923. The body portion 920 sandwiches and holds the first sliding portion 923a and the protruding portion 923c such that the notched portion 920d may abut on the protruding portion 923c.

When the detachable button 923 is pressed toward the body portion 920 in the mounting member 9, the spring member 922 is deformed and an end portion expands. When the spring member 922 expands, the locking protrusion 921 may move in the direction of separating from the paired locking protrusion 921. In this state, the eyepiece unit 232 may be attached or detached. When the pressing state of the detachable button 923 is released, the spring member 922 returns to the state before deformation. When the spring member 922 returns to the state before deformation, the locking protrusion 921 protrudes toward the paired locking protrusion 921 and is locked to the eyepiece unit 232. In this state, the locking protrusion 921 is in pressure-contact with the eyepiece unit 232, and thus, the eyepiece unit 232 is regulated from being detached from the mounting member 9.

In the above-described embodiment, the body portion 920 is provided with the guide portion that guides the movement of the detachable button 923, and the detachable button 923 is provided with the sliding portion that slides along the guide portion in the mounting member 9, and the body portion formed of one member holds the locking protrusion 921, the spring member 922, and the detachable button 923 to control a biasing state of the locking protrusion 921. According to the present embodiment, since the body portion is formed of one member, it is possible to reduce the number of parts constituting the member while maintaining the function of the mounting member 9.

In addition, in the embodiment, the detachable button 923 has the arc shape and sandwiches the spring member 922 with the body portion 920 to suppress the exposure of the spring member 922 to the outside in the mounting member 9. If the spring member 922 is exposed to the outside, the locking protrusion 921 is not properly biased so that the body portion 920, the user's finger, or the like is sometimes damaged. Since the detachable button 923 suppresses the exposure of the spring member 922 in the present embodiment, it is possible to maintain an appropriate biasing state of the locking protrusion 921 and prevent the above-described damage.

Incidentally, the configuration in which the protruding portion 923c is provided on the detachable button 923 and the protruding portion 923c is locked with the notched portion 920d of the body portion 920 in order to lock the detachable button 923 with the body portion 920 has been given as an example in the embodiment. However, the present disclosure is not limited to this configuration as long as the detachment of the detachable button 923 from the body portion 920 may be suppressed. For example, a protruding portion may be provided on the first sliding portion or the second sliding portion so as to be locked with the body portion, or it may be configured such that a protruding portion is provided on the body portion, and this protruding portion is locked with the detachable button.

In addition, the description has been given in the embodiment regarding the example in which the body portion 920 is provided with the two guide portions (first guide portion 920b and second guide portion 920c) and the detachable button 923 is provided with the sliding portions (first sliding portion 923a and second sliding portion 923b) that slide on the respective guide portions to guide the moving direction of the detachable button 923. However, it may be configured such that only one combination between a combination of the first guide portion 920b and the first sliding portion 923a and a combination of the second guide portion 920c and the second sliding portion 923b is provided.

Other Embodiments

Variations may be formed by appropriately combining a plurality of components disclosed in the endoscopic device according to the above-described embodiment of the present disclosure. For example, some components may be deleted from all the components described in the endoscopic device according to the above-described embodiment of the present disclosure. Further, the components described in the endoscopic devices according to the above-described embodiment and modifications of the present disclosure may be appropriately combined.

Although some of the embodiments of the present application have been described in detail with reference to the drawings as above, these are merely examples, and it is possible to carry out the present disclosure in other forms in which various modifications and improvements have been made based on the knowledge of those skilled in the art, including the aspects described in the disclosure.

Incidentally, the present technique may also adopt the following configurations.

(1)

A mounting member including:

a body portion provided in a camera head including an image sensor, the body portion being rotatable about a first axis that passes through the body portion and connectable with an endoscope;

a locking protrusion provided in the body portion and configured to lock with the endoscope;

a detachable button configured to be movable with respect to the body portion and control attachment and detachment of the endoscope to and from the body portion; and a spring whose load applied to the locking protrusion changes according to an advancing/retreating operation of the detachable button with respect to the body portion, wherein the detachable button includes a sliding portion extending in an advancing/retreating direction with respect to the body portion and configured to slide with respect to the body portion, and the body portion includes a guide portion configured to guide a moving direction of the sliding portion.

(2)

The mounting member according to (1), wherein the detachable button includes a protruding portion configured to protrude in a moving direction of the detachable button, and the body portion includes a notched portion having a hole shape with which the protruding portion is locked.

(3)

The mounting member according to (1), wherein the detachable button includes a sliding portion extending in a moving direction of the detachable button and configured to slide on the body portion, and the body portion includes a concave-shaped guide portion configured to guide a moving direction of the sliding portion.

(4)

The mounting member according to (1), wherein the detachable button includes two sliding portions each extending at each of both ends of the detachable button, and the body portion includes two concave-shaped guide portions each configured to guide a moving direction of each of the sliding portions.

(5)

The mounting member according to (1), wherein the detachable button includes:

a first sliding portion extending in a moving direction of the detachable button and configured to slide on the body portion; and two second sliding portions each extending at each of both ends of the detachable button, and the body portion includes:

a concave-shaped first guide portion configured to guide a moving direction of the first sliding portion; and two concave-shaped second guide portions each configured to guide a moving direction of each of the second sliding portions.

(6)

An endoscopic device comprising:

the mounting member according to (1); and an endoscope configured to capture and emits a subject image.

As described above, the mounting member and the endoscopic device according to the present disclosure are advantageous in terms of reducing the number of parts.

According to the present disclosure, it is possible to reduce the number of parts.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A mounting member comprising:

a body connectable to a camera head, the camera head including an image sensor, the body being rotatable about a first axis that passes through the body and the body being connectable with an endoscope;

a locking protrusion in the body and configured to lock with the endoscope;

a detachable button configured to be movable with respect to the body, the detachable button being configured to control attachment and detachment of the endoscope to and from the body; and a spring whose load applied to the locking protrusion changes according to an advancing/retreating operation of the detachable button with respect to the body, wherein the detachable button includes a slider extending in an advancing/retreating direction with respect to the body and configured to slide with respect to the body, and the body includes a guide configured to guide a moving direction of the slider.

2. The mounting member according to claim 1, wherein the detachable button includes a protrusion configured to protrude in a moving direction of the detachable button, and the body includes a notch having a hole shape with which the protrusion is locked.

3. The mounting member according to claim 2, wherein the spring is a leaf spring and the locking protrusion includes a locking protrusion at either end of the leaf spring.

4. The mounting member according to claim 3, wherein the spring includes two leaf springs facing each other across the first axis in a second direction orthogonal to the first axis and the locking protrusions form two pairs of locking protrusions that face each other across the first axis in a third orthogonal to the second direction.

5. The mounting member according to claim 1, wherein the body includes a concave-shaped guide extending in a moving direction of the detachable button and configured to guide the slider.

6. The mounting member according to claim 1, wherein the slider includes a pair of sliders, each slider extending at each of both ends of the detachable button, and the body includes two concave-shaped guides each configured to guide each of the sliders.

7. The mounting member according to claim 1, wherein the slider includes:

a first slider extending in a moving direction of the detachable button and configured to slide on the body; and two second sliders each extending at each of both ends of the detachable button, and the body includes:

a concave-shaped first guide configured to guide the first slider; and two concave-shaped second guide guides each configured to guide each of the second sliders.

8. An endoscopic device comprising:

the mounting member according to claim 1; and an endoscope configured to emit a subject image.

9. The endoscopic device according to claim 8, further comprising:

a camera head configured to capture the subject image, the mounting member being between the endoscope and the camera head.

10. The endoscopic device according to claim 8, further comprising a support configured to attach the mounting member to the camera head and to support rotation of the body.

11. The mounting member according to claim 1, further comprising a support configured to attach the mounting member to the camera head and to support rotation of the body.

12. The mounting member according to claim 11, wherein the support extends along the first axis through the body.

13. The mounting member according to claim 12, wherein the support includes a first end to connect to the camera head and a second end connected to a regulator.

14. The mounting member according to claim 1, wherein the detachable button has an arc shape.

15. The mounting member according to claim 14, wherein the spring is a leaf spring and the detachable button sandwiches the spring with the body.

16. The mounting member according to claim 1, wherein the detachable button includes a pair of detachable buttons that face each other with the first axis there between.

17. The mounting member according to claim 1, wherein the detachable button includes a first connector, and the body includes a second connector configured to mate with the first connector, wherein the first and second connectors are locked when mated.

18. The mounting member according to claim 1, wherein the detachable button sandwiches the spring with the body and the load of the spring changes according to operation of the detachable button with respect to the body.

* * * * *